United States Patent
Fagan et al.

[11] Patent Number: 6,113,557
[45] Date of Patent: Sep. 5, 2000

[54] VARIABLE STIFFNESS ANGIOPLASTY GUIDE WIRE

[75] Inventors: John R. Fagan, Pepperell; Richard Choh, Lowell; Richard Morrill, Billerica, all of Mass.

[73] Assignee: Medtronic AVE, Inc., Santa Rosa, Calif.

[21] Appl. No.: 08/879,569

[22] Filed: Jun. 20, 1997

[51] Int. Cl.[7] .................................................... A61B 5/00
[52] U.S. Cl. ......................... 600/585; 600/433; 600/434; 600/462
[58] Field of Search .................................. 600/434, 439, 600/585, 462, 463, 466, 467, 433; 604/96, 280

[56] References Cited

U.S. PATENT DOCUMENTS

| | | | |
|---|---|---|---|
| Re. 34,466 | 12/1993 | Taylor et al. ............................. | 600/434 |
| 4,215,703 | 8/1980 | Willson . | |
| 4,676,249 | 6/1987 | Arenas et al. ............................ | 600/585 |
| 4,719,924 | 1/1988 | Crittenden et al. . | |
| 4,827,941 | 5/1989 | Taylor et al. . | |
| 4,873,983 | 10/1989 | Winters . | |
| 4,886,067 | 12/1989 | Palermo .................................. | 600/585 |
| 4,961,433 | 10/1990 | Christian . | |
| 5,040,543 | 8/1991 | Badera et al. ........................... | 600/585 |
| 5,052,404 | 10/1991 | Hodgson . | |
| 5,065,769 | 11/1991 | De Toledo .............................. | 602/282 |
| 5,069,217 | 12/1991 | Fleischhacker, Jr. ................... | 600/434 |
| 5,174,295 | 12/1992 | Christian et al. ....................... | 600/585 |
| 5,273,052 | 12/1993 | Kraus et al. . | |
| 5,372,144 | 12/1994 | Mortier et al. . | |
| 5,404,887 | 4/1995 | Prather ................................... | 600/434 |
| 5,480,382 | 1/1996 | Hammerslag et al. ................. | 600/585 |
| 5,497,782 | 3/1996 | Fugoso ................................... | 600/585 |
| 5,542,434 | 8/1996 | Imran et al. . | |
| 5,562,275 | 10/1996 | Weissenfluh et al. . | |
| 5,605,162 | 2/1997 | Mirzaee et al. . | |
| 5,722,424 | 3/1998 | Engelson ................................ | 600/585 |
| 5,762,615 | 6/1998 | Weier ..................................... | 600/585 |

*Primary Examiner*—Richard J. Apley
*Assistant Examiner*—Justine R. Yu
*Attorney, Agent, or Firm*—Sterne Kessler Goldstein & Fox P.L.L.C.

[57] ABSTRACT

An angioplasty guidewire includes a proximal shaft and an intermediate section extending from the shaft to a distal joint and having a stiffener and a flexible member. The stiffener and the flexible member are disposed in coaxial slidable relationship and operable, as the stiffener and flexible member undergo relative axial shifting, to cooperatively impart a variable stiffening force on the intermediate section. A flexible distal tip mounts to the end of the intermediate section and projects axially therefrom.

15 Claims, 5 Drawing Sheets

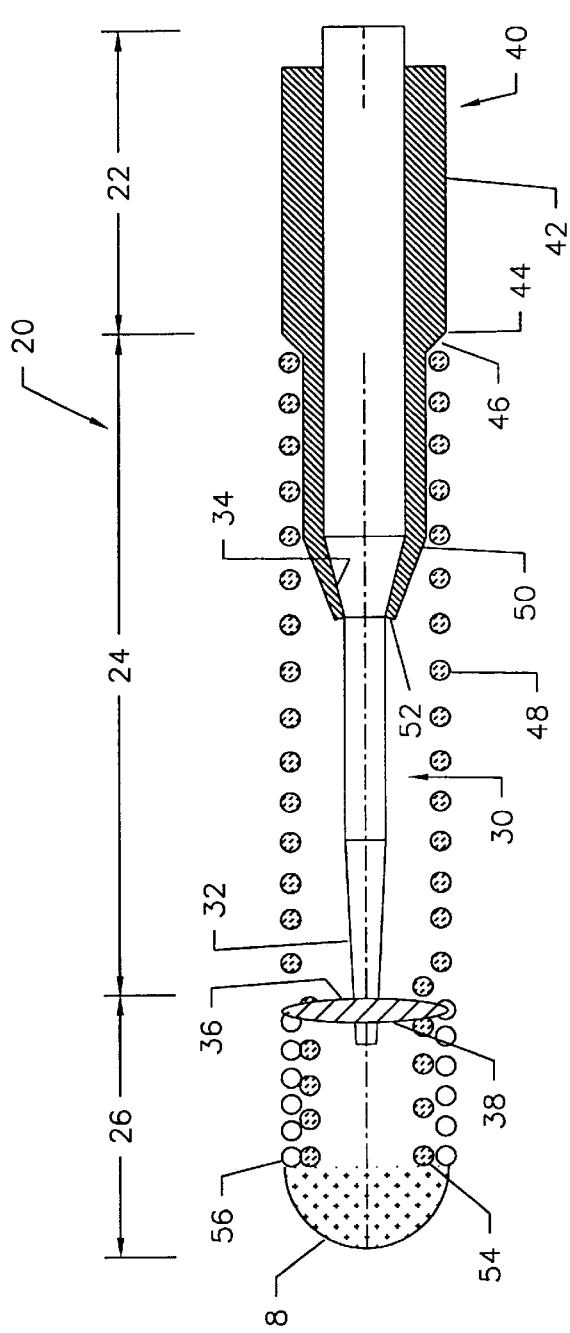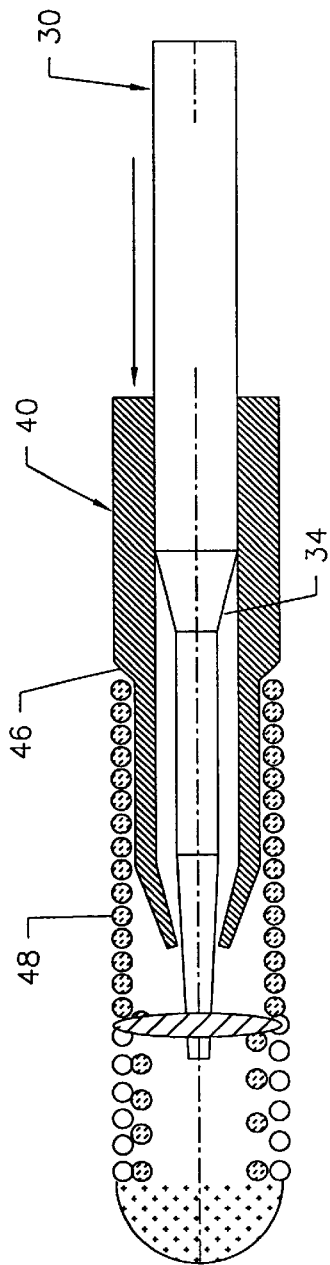
FIG 2
FIG 3

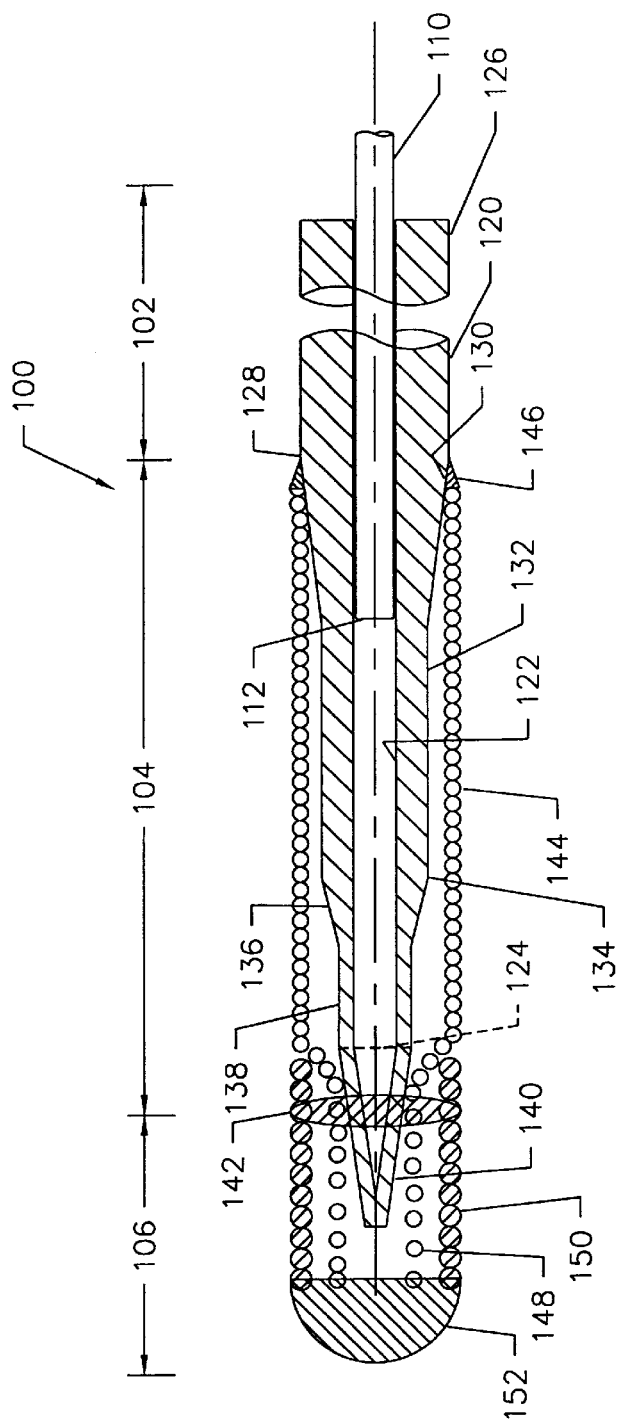
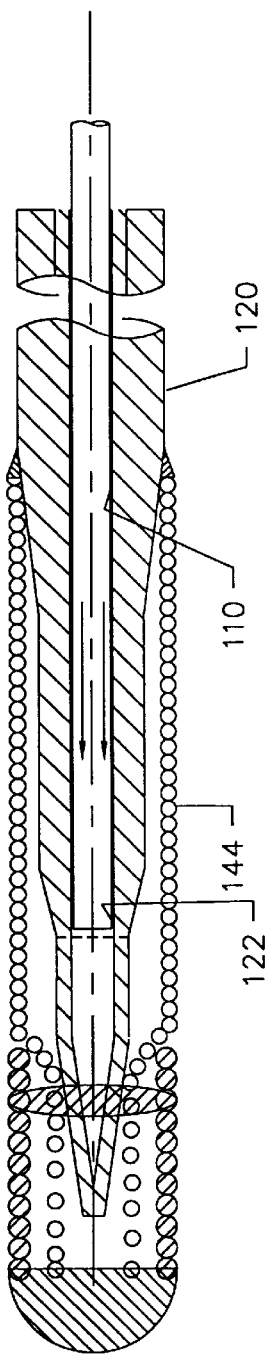
FIG 8
FIG 9

VARIABLE STIFFNESS ANGIOPLASTY GUIDE WIRE

FIELD OF THE INVENTION

The invention relates to guide wires used in angioplasty procedures and more particularly an angioplasty guide wire having shiftable control elements to provide a variable stiffness capability.

BACKGROUND OF THE INVENTION

Treatments for cardiovascular conditions caused by restricted or blocked blood vessels increasingly involve trauma minimizing non-invasive surgical techniques. For example, in an angioplasty procedure, an elongated and relatively thin catheter can treat a blood vessel restriction, commonly referred to as a stenosis or occlusion, by advancing through the vessel to a location proximate the restriction. A balloon disposed distally on the end of the catheter radially expands against the restriction to open the vessel for increased bloodflow. However, because many angioplasty catheters comprise "over the wire" designs, in order for the catheter to reach the stenosed location, a guide wire typically must first define the vascular path.

Conventional angioplasty guide wires typically include a proximal shaft comprising a solid wire or a solid wall tube with an outer diameter equal to the nominal size of the guide wire. The shaft primarily functions to guide and support a catheter, and to smoothly transmit rotation from the proximal end to an intermediate section. The intermediate section extends axially from the proximal shaft and generally comprises a tapered core wire surrounded by a coiled spring and typically has more flexibility than the proximal shaft. Like the proximal shaft, the intermediate section must assist in guiding the catheter and smoothly transmitting rotation. However, some degree of flexibility in the intermediate section is desirable to conform the catheter to the curvature of the aortic arch and the coronary arteries. Extending from the intermediate section at a distal joint is a flexible distal tip that accepts a pre-formed curved shape resembling a "J". The curved tip tends to steer the guide wire in the direction of the hook.

To reach a blood vessel restriction, conventional guide wires typically traverse tortuous paths having relatively sharp turns and passage constrictions. A common technique to aid in steering the guide wire, especially where the path branches into a plurality of passages, involves rotating the shaft to redirect the pre-formed "J" towards a particular branch, then advancing the wire once the correct orientation is achieved. Unfortunately, as the wire advances into blood vessels of reduced diameter, the friction generated between the guide wire and the inner walls of the vessel tends to inhibit rotation from the proximal shaft, through the intermediate section to the distal tip. Consequently, overly flexible intermediate sections are susceptible to substantial twisting and doubling over, thereby failing to transmit the desired rotation to the distal end of the guide wire.

Another problem faced by conventional guide wires involves supporting the catheter once the correct position is reached. Typically, after the guide wire is positioned, an exchange is made whereby the relatively flexible shaft is replaced by a relatively stiff shaft with a portion of the guide wire remaining in place. Although conventionally exchanging wires is a commonplace practice, the procedure undesirably adds steps in the overall procedure, and exposes the insertion area to potential contamination.

One proposal for providing an angioplasty guide wire with a controllably variable stiffness is disclosed in U.S. Pat. No. 4,676,249 to Arenas. The guide wire includes an elongated core wire and a tubular stiffening member movable within the lumen of a flexible coiled wire body defining a distal end of the guide wire. Varying degrees of flexibility are possible at the distal end by shifting the relative positions of the core wire and/or the tubular stiffening member in the wire body. U.S. Pat. No. 4,873,983 to Winters teaches a similar device that includes a tapered core wire moveable within the distal end of an outer tube to steer the distal end of the tube through a vasculature.

In both the Arenas and Winters devices, the respective stiffening features affect only the distal ends of the guide wires. Thus, support in the intermediate section of the guide wire, for example, to assist tracking of a stent catheter, is unavailable. A further disadvantage of the above-described devices involves the lack of torsional support provided by the stiffening member to ensure full rotational transmission through the wires to effect proper steering in relatively constrained blood vessels.

Another approach, disclosed in U.S. Pat. No. 5,542,434 to Imran, involves a guide wire having a core wire and a hypotube coaxially disposed around the core wire. An actuator wire formed of a memory material runs longitudinally with the core wire at the distal end of the guide wire to stiffen in response to thermal energy supplied by a heater. The core wire and hypotube are bonded together by an adhesive to prevent relative axial or torsional displacement.

While the Imran device provides a relatively stiff guide wire for purposes of torque control, such stiffness at the proximal and intermediate sections of the guide wire is permanent, and not selectively controllable. Thus, like the Arenas and Winters devices described above, the variable stiffening feature is limited to the distal end of the guide wire. Moreover, the stiffness is controllable only through use of a relatively complex and costly thermal mechanism requiring additional wires running the length of the guide wire.

Therefore, the need exists for an angioplasty guide wire having controllable elements that cooperate to provide a variable stiffness in the intermediate section of the guide wire. Moreover, the need also exists for such a guide wire having a selective locking mechanism to provide enhanced torsional control during insertion of the catheter through a vasculature. The guide wire of the present invention satisfies these needs.

SUMMARY OF THE INVENTION

The guide wire and method of the present invention provides the capability of controllably changing the stiffness of the intermediate section while the guide wire remains in vivo. This eliminates the need to exchange guide wire elements when added support is necessary for particular procedures. Moreover, the elements may be locked in some circumstances to maximize torsional transmission during advancement of the guide wire through constricted vascular passages.

To realize the above advantages, the present invention, in one form, comprises an angioplasty guidewire including a proximal shaft and an intermediate section extending longitudinally from the shaft to a distal joint and including a stiffener and a flexible member. The stiffener and flexible member are disposed in coaxial slidable relationship and operable, as the stiffener and flexible member undergo relative axial shifting, to cooperatively impart a variable stiffening force on the intermediate section. A flexible distal tip mounts to the end of the intermediate portion and projects axially from the intermediate section.

In another form, the invention comprises an angioplasty catheter system including an angioplasty catheter having an expandable element for dilating radially outwardly inside a blood vessel and a controllably variable guide wire. The guide wire comprises a proximal shaft and an intermediate section extending longitudinally from the shaft to a distal joint and including a stiffener and a flexible member. The stiffener and flexible member are disposed in coaxial slidable relationship and operable, as the stiffener and flexible member undergo relative axial shifting, to cooperatively impart a variable stiffening force on the intermediate section. A flexible distal tip is mounted to the end of the intermediate portion and projects axially therefrom.

In yet another form, the invention comprises a method of deploying a guide wire through a vasculature to a restricted location in a blood vessel. The guide wire includes a flexible member and a stiffener coaxially disposed slidably with the flexible member. The flexible member and the stiffener are initially positioned in an intermediate section to effect a predetermined flexibility in the intermediate section. The method includes the steps of first inserting the guide wire through an incision accessing said vasculature, then threading the guide wire through the vasculature to the restricted location. The method then proceeds with the step of stiffening the intermediate section by axially displacing the stiffener with respect to the flexible member sufficient to support a dilatation catheter.

Other features and advantages of the present invention will be apparent from the following detailed description when read in conjunction with the accompanying drawings.

BRIEF DESCRIPTION OF THE DRAWINGS

FIG. 2 is a partial longitudinal sectional view of a guide wire according to a first embodiment of the present invention;

FIG. 3 is a partial longitudinal sectional view similar to FIG. 2;

FIG. 8 is a partial longitudinal sectional view of a guide wire according to a fourth embodiment of the present invention; and FIG. 9 is a partial longitudinal sectional view similar to FIG. 8.

DETAILED DESCRIPTION OF THE INVENTION

Figure 1:
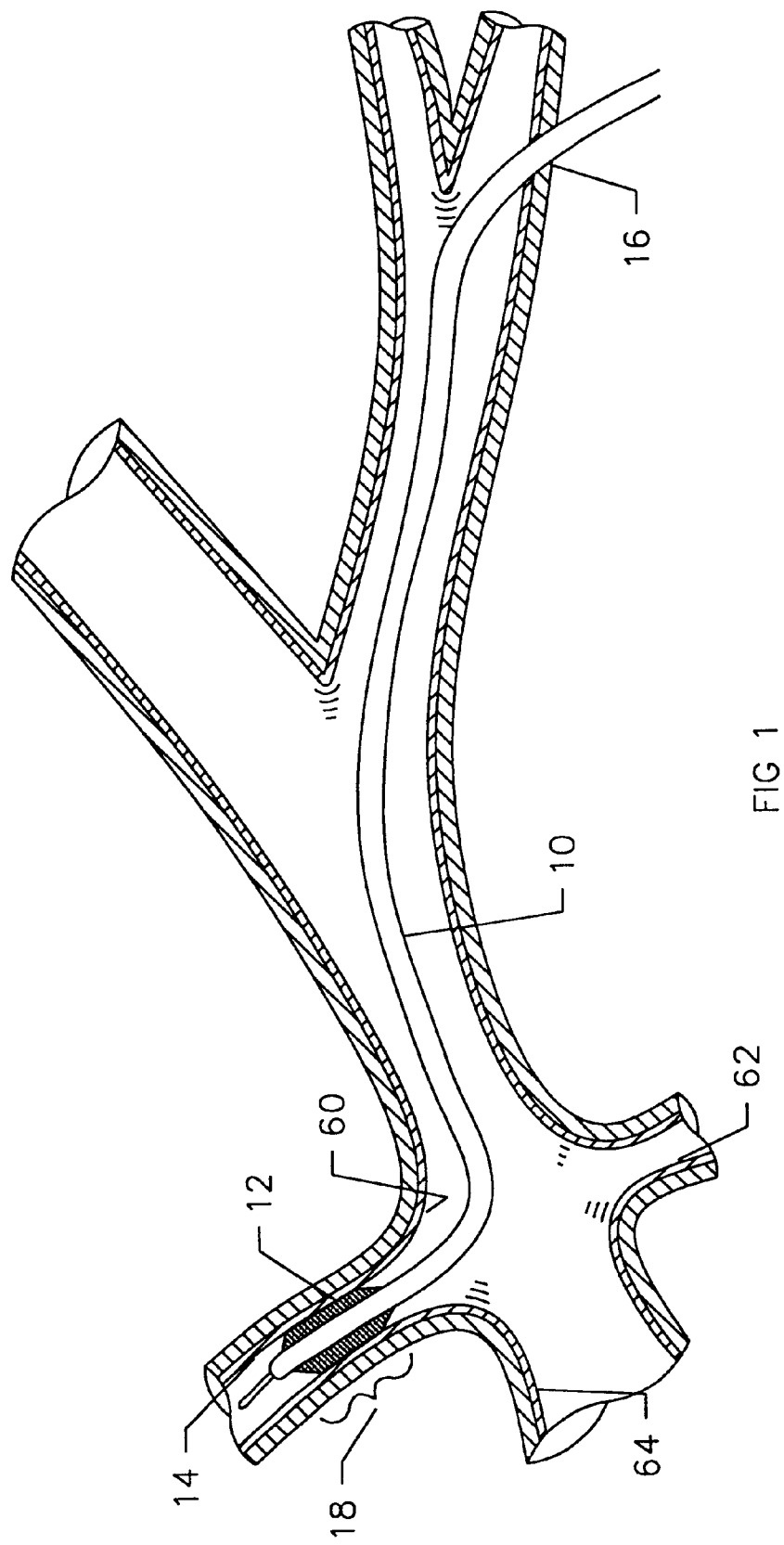
FIG. 1 is a partial diagrammatical view of a catheter system according to one embodiment of the present invention.

Angioplasty catheter systems and procedures enable operators to perform life-saving treatments with minimal tissue trauma experienced by the patient. Referring now to FIG. 1, an angioplasty catheter 10 of the "over the wire" design having a radially expandable balloon 12 is shown positioned within a branch blood vessel 14. From the point of entry, typically an incision made at 16, to the eventual destination 18, the catheter must traverse a winding, branch laden path. As a result, the catheter must rely on a relatively flexible guide wire to establish the path for the catheter to track.

Referring now to FIGS. 2 and 3, a guide wire in accordance with a first embodiment of the present invention, generally designated 20, provides variable stiffness capability in vivo and includes a flexible member 30 moveable relative to a stiffener 40 that longitudinally extends along respective guide wire segments defining a proximal shaft 22, an intermediate section 24, and a distal portion 26.

The flexible member 30 comprises a core wire formed of a relatively flexible strand of stainless steel measuring about 180 centimeters and having a relatively constant diameter over a majority of its length. Typically, the diameter ranges from about 0.005 inches to 0.01 inches, depending upon the application involved. Respective primary and secondary tapers 32 and 34 are formed in the core wire along the intermediate section to narrow the core wire and provide added flexibility. A distal end 36 of the core wire terminates in a bonded distal joint 38 that connects the intermediate section 24 the distal portion 26 of the guide wire.

With continuing reference to FIGS. 2 and 3, the stiffener 40 comprises a formed hypotube that coaxially extends longitudinally along the core wire 30 in slidable relationship therewith. The hypotube is formed with a relatively stiff shaft section 42 that narrows down, at 44, to define a shoulder 46 for mounting one end of an intermediate spring 48. The other end of the spring projects axially beyond the distal joint 38 and defines an inner spring 54 that terminates at a distal tip 58. The narrowed section of the hypotube provides somewhat more flexibility than the stiff shaft section and tapers radially inwardly at 50 to form a restricted mouth 52 for complementally engaging the core wire secondary taper 34. The mouth and the secondary taper cooperate to form an axially and radially inhibiting friction fit.

The proximal shaft 22 and the intermediate section 24 together comprise various lengths of the core wire 30 and the hypotube 40. However, for convention purposes, the intermediate spring 48 typically defines the guide wire intermediate section. Thus, under this convention, the proximal shaft 22 extends from the proximal end of the guide wire (not shown), to the annular shoulder 46 formed in the slidable hypotube 40.

Further referring to FIG. 2, the distal portion 26 extends axially from the distal joint 38 and includes respective inner and outer coil springs 54 and 56 disposed concentrically and interposed between the distal joint 38 and the distal tip 58. The tip typically retains a pre-formed "J" shape (not shown) to urge the guide wire in desired directions and thereby assist in steering the catheter during insertion through the vasculature.

Assembly of the guide wire 20 is well within the level of skill in the art, and generally includes first sliding the core wire 30 through the length of the hypotube 40 until the restricted mouth 34 frictionally engages the secondary taper 34. The intermediate spring 48 is then run over the uncovered portion of the core wire projecting outwardly from the distal tip of the hypotube and attached to the annular shoulder 46 with a suitable adhesive. The distal joint 38 is then formed at the tip of the core wire 30 to confine the intermediate spring therearound with a globule of solder material or the like. With the inner spring 54 projecting axially from the intermediate spring, the outer spring 56 is slid coaxially over the inner spring and then bonded to the distal joint with adhesive. Next, the opposite ends of the springs are capped by mounting the hemispherical tip 58. Following assembly, the guide wire is typically packaged separately in a sterile container for use in an angioplasty catheter system.

Referring now to FIGS. 1, 2 and 3, during operation, the guide wire 20 is typically first removed from its sterile packaging and inserted into the vascular system through the small external incision 16. Initial advancement of the guide wire through the body requires a relatively high degree of flexibility at the distal portion 26 of the guide wire, with a moderate level of flexibility at the intermediate section 24. To maximize available flexibility at the distal portion, the hypotube 40 conveniently frictionally locks to the core wire 30 by sliding the hypotube rearwardly to engage the complementally formed mouth 52 and secondary taper 34.

Locking of the core wire 30 to the hypotube 40 also serves to maximize the transmission of torque from the proximal end 22 of the guide wire to the intermediate section 24 by integrating the core wire and hypotube into a relatively large diameter rod, rather than a substantially thin wire. Those skilled in the art will appreciate this feature to substantially assist the operator in steering the guide wire 20 through the vasculature.

For example, as shown in FIG. 1, a typical path for the guide wire 20 to traverse often includes sharp turns such as at 60, and branch points leading to a plurality of branch paths, such as at 62 and 64. The guide wire may be conveniently steered and threaded along the path by rotating the entire assembly to orient the pre-formed "J" (not shown) such that the hook points in a desired direction. However, as the blood vessels become more constrained, rotation of the guide wire along the 180 centimeter length becomes more difficult, and even stops altogether unless the proximal, intermediate and distal portions have a relatively high torsional stiffness. Under such circumstances, the operator merely locks the hypotube 40 and the core wire 30 together to achieve the added torsional stiffness necessary to permit rotation of the guide wire in constrained areas.

Once the guide wire 20 is successfully threaded in position, the operator may then choose to stiffen the intermediate section 24 by sliding the hypotube 40 distally to provide axial support near the treatment area. Advancement of the hypotube distally along the core wire, as shown in FIG. 3, compresses the intermediate spring while bringing more of the relatively stiff shaft section of the hypotube into the intermediate section of the guide wire. The net result is a cooperative stiffening of the intermediate section by the interaction of the hypotube with the core wire. With the added axial support, the balloon or stent catheter 10 may track the guide wire 20 and treat the location without undesirable overflexing at the intermediate section of the guide wire. Following the treatment, the hypotube may be shifted back to its initially locked position to enable swift withdrawal of the guide wire from the body.

Figure 4:
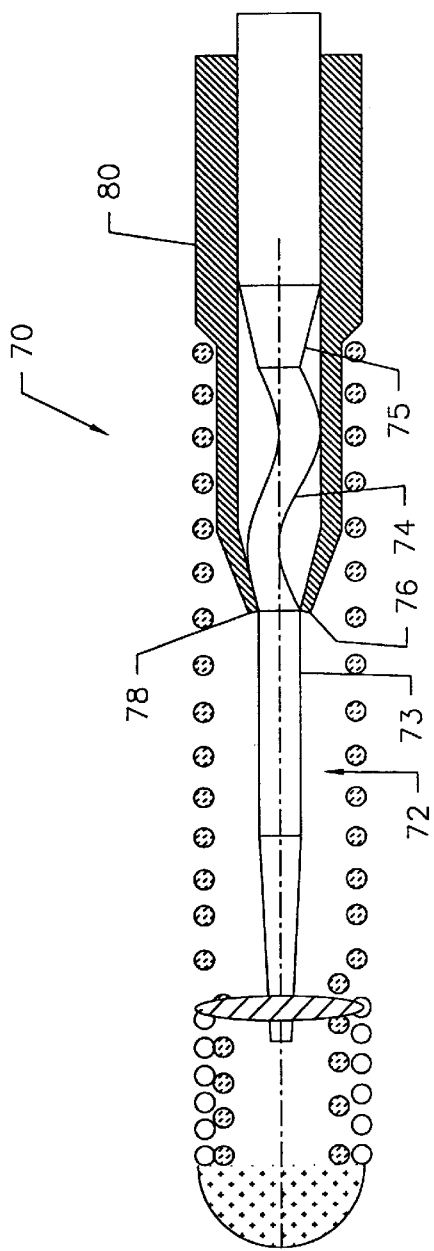
FIG. 4 is a partial longitudinal sectional view of a guide wire according to a second embodiment of the present invention.
Figure 5:
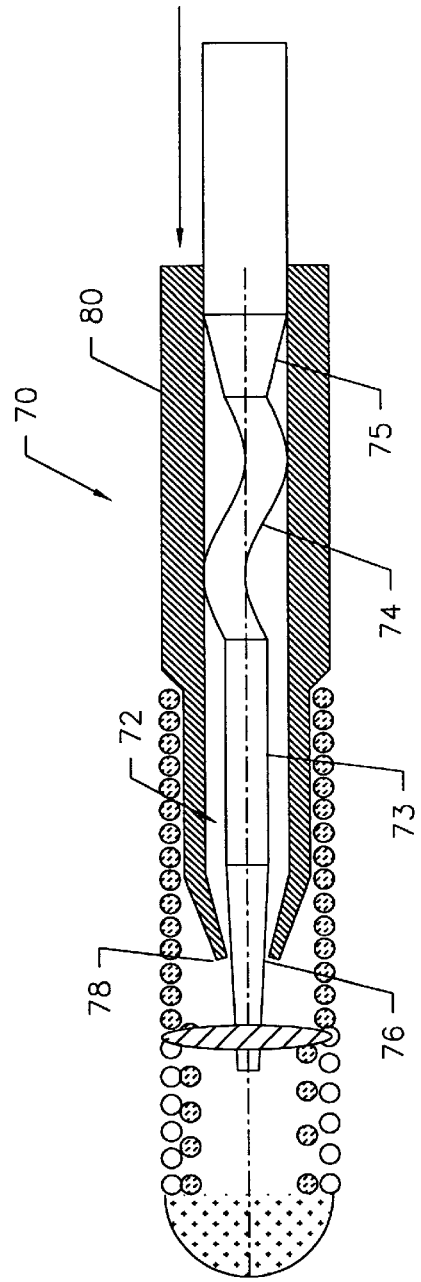
FIG. 5 is a partial longitudinal sectional view similar to FIG. 4.

Referring now to FIGS. 4 and 5, a guide wire in accordance with a second embodiment of the present invention, generally designated 70, is formed substantially similar to the first embodiment albeit with a modified core wire 72 construction. The core wire includes a sawtooth waveshaped diametrically offset portion 74 disposed between a secondary barrel 73 and a secondary taper 75. The offset portion provides a friction fit when engaged with an internal radial surface 76 in a hypotube 80.

In operation, the guide wire 70 functions in much the same manner as the first embodiment, but provides a locking friction fit over a greater range of hypotube positions. FIG. 4 illustrates a locked position, while the stiffening action of the hypotube shifted axially is shown in FIG. 5.

Figure 6:
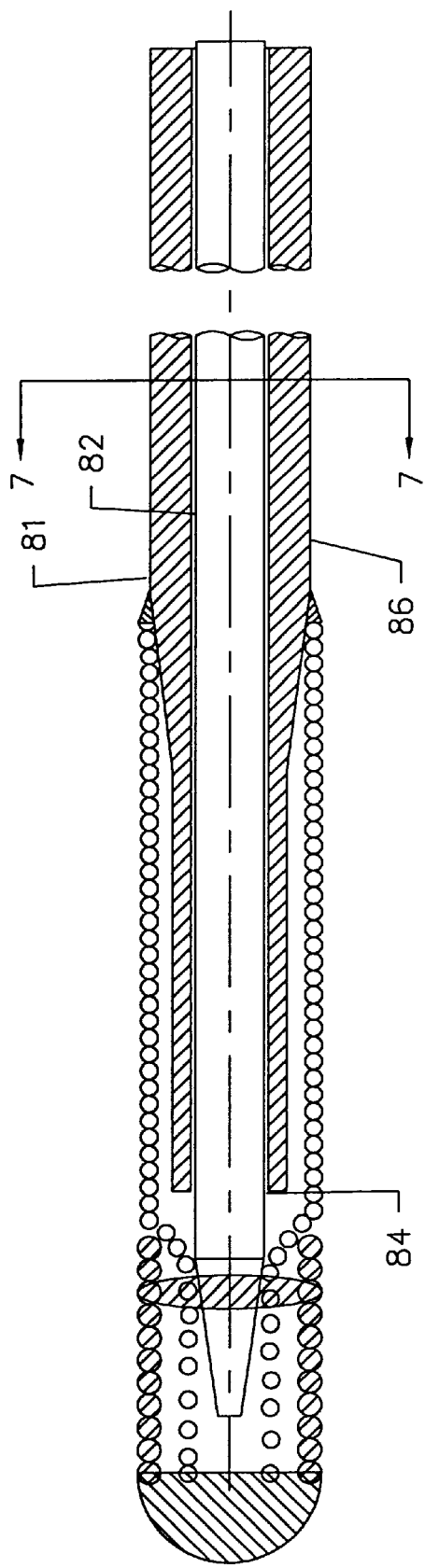
FIG. 6 is a partial longitudinal sectional view of a guide wire according to a third embodiment of the present invention.
Figure 7:
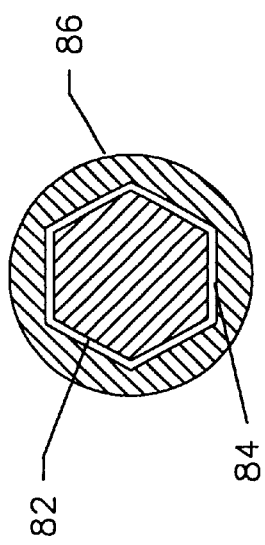
FIG. 7 is an axial cross sectional view along lines 7—7 of FIG. 6.

Referring now to FIGS. 6 and 7, in yet another embodiment, a guide wire 81 is formed substantially similar to the aforedescribed embodiments albeit with a modified core wire/hypotube construction. The guide wire includes a core wire 82 formed with a polygonal cross-section, such as a hexagonal or pentagonal shape. An inner surface 84 of a hypotube 86 is complementally formed with the same polygonal shape to axially receive the formed core wire.

Operation of the modified core wire/hypotube embodiment is also similar to the previously described embodiments. However, unlike the prior constructions, which included a selectively engageable locking mechanism to effect enhanced torsional stiffness, the modified construction provides continuous torsional support. During positional maneuvering of the guide wire, rotation of the hypotube 86 rotates the inner wire 82 due to the complementally formed polygonal surfaces thereby transmitting any applied torque from the proximal end to the tip and directing the J-shaped tip into the desired branch of the artery.

With reference to FIGS. 8 and 9, a guide wire in accordance with a fourth embodiment of the present invention, and generally designated 100, includes a stiffener 110 slidably received within a closed ended flexible member 120 that longitudinally extends along respective segments defining a proximal shaft 102, an intermediate section 104, and a distal portion 106.

The stiffener 110 comprises a core wire formed of an elongated thin rod of tungsten/stainless steel alloy having a diameter within the range of 0.004 inches to 0.009 inches and a length of approximately 180 centimeters. Unlike the first and second embodiments, the core wire diameter remains constant with the distal tip truncated in a flat engagement end 112.

Further referring to FIG. 8, the flexible member 120 comprises a formed hypotube including a relatively flexible tubular body formed with an interior blind bore 122 having a constant internal diameter to slidably receive the core wire 110 and a distal wall 124 to serve as a stop. The exterior of the hypotube includes a major diameter 126 extending most of the hypotube length. The major diameter narrows at 128 along a secondary taper 130 and ends in a secondary barrel 132. The secondary barrel extends longitudinally to 134 where it begins to fall off in a primary taper 136 that extends to a primary barrel 138. The end of the hypotube is swaged down into a tapered section 140 that bonds to a distal joint 142.

With further reference to FIG. 8, an intermediate spring 144 telescopically receives the hypotube 120 and bonds to the secondary taper 130 through the use of a suitable adhesive that forms an adhesive joint 146. The opposite end of the spring connects to the distal joint 142. Unlike the first and second embodiments, the intermediate spring 144 lies mounted in an axially fixed position.

The distal portion 106 is formed substantially similar to the first and second embodiments. An inner spring 148 is formed integrally with the intermediate spring and projects axially distally. The inner spring tapers radially inwardly and then forms a constant diameter in an axially expanded configuration to provide a larger pitch. An outer spring 150 coaxially confines the inner spring and bonds with the inner spring to the distal point 142. A hemispherical cap 152 bonds to the ends of the springs.

Assembly of the guide wire 100 involves first inserting the intermediate spring 144 over the distal end of the hypotube 120 and bonding one end of the spring to the secondary taper at 154. The other end of the spring is then bonded or soldered to the distal joint 142, along with the distal end of the hypotube itself, and the respective inner and outer springs 148 and 150. The cap 152 is then attached to the opposite end of the springs and pre-formed with the springs to take on a "J"-shape (not shown). The core wire 110 is then inserted through the length of the hypotube.

Referring to FIGS. 8 and 9, during operation, the guide wire 100 is initially inserted into the vasculature with the core wire 110 somewhat retracted from the end of the hypotube 120 to maximize the flexibility of the assembly during advancement along winding vessels. In relatively constricted areas where turns must be artfully negotiated, the operator merely rotates the hypotube shaft to effect a corresponding rotation at the distal portion 106, thereby re-orienting the distal "J", and urging the guide wire along another direction. Because of the relatively large diameter of the hypotube 120, the transmission of rotation of the assembly from the proximal end to the intermediate section is substantially unaffected.

Once positioned at the treatment site, the guide wire stiffness may be increased by conveniently sliding the core wire 110 through the hypotube bore 122 toward the formed stop 124. Advancement of the core wire distally results in a cooperation between the core wire and the hypotube to impart a varying stiffness corresponding to the depth of insertion of the core wire through the hypotube bore 122. Depending upon the application, the guide wire will reflect a level of stiffness necessary to properly support a balloon or stent catheter. When the procedure is completed, the core wire may be removed to restore flexibility to the guide wire so that it may be quickly removed.

Those skilled in the art will appreciate the many benefits and advantages afforded by the present invention. Of significant importance is the controllable axial stiffness feature requiring merely relative axial displacement of the core wire with respect to the hypotube to vary the flexibility of the guide wire in vivo. This feature eliminates the need to effect any exchange in hardware preliminary to the actual stent delivery or balloon expansion step.

The invention also offers an important advantage in allowing the operator to adjust the torsional stiffness during operation merely by locking the hypotube and core wire together (as in the first and second embodiments), or through the inherent nature of the hypotube design itself (third embodiment). Such an advantage permits reliable rotational steering of the guide wire through the vascular system with minimal torsional interference caused by constricted blood vessels and the like.

While the invention has been particularly shown and described with reference to the preferred embodiments thereof, it will be understood by those skilled in the art that various changes in form and detail may be made therein without departing from the spirit and scope of the invention.

What is claimed is:

1. An angioplasty guidewire comprising:

a proximal shaft for insertion into a patient's body and having a distal end;

an intermediate section extending axially outwardly from said distal end of said shaft to a distal joint, said intermediate section including a spring coil, a stiffener extending from said proximal shaft, and a flexible member, said stiffener being coaxially disposed over said flexible member and said stiffener and said flexible member being slidable relative to each other to cooperatively impart a variable stiffness to said intermediate section, said variable stiffness being increased by advancing said stiffener over said flexible member toward said distal joint, said variable stiffness being reduced by moving said stiffener over said flexible member away from said distal joint; and a flexible distal tip mounted to an end of said intermediate portion at said distal joint and projecting axially therefrom.

2. A guidewire according to claim 1 wherein said intermediate portion further includes:

a locking mechanism for selectively inhibiting relative movement between said flexible member and stiffener to enhance rotational transmission between said proximal shaft and said distal tip.

3. A guidewire according to claim 1 wherein:

said stiffener comprises a hypotube; and said flexible member comprises a resilient core wire.

4. A guidewire according to claim 3 wherein:

said core wire is fixed to said distal tip.

5. A guidewire according to claim 4 wherein:

said hypotube includes a formed distal open end tapered radially inwardly; and said core wire includes a medial tapered portion complementally formed to effect a friction fit with said hypotube tapered end and define said clamping device.

6. A guidewire according to claim 4 wherein:

said proximal shaft includes a formed passage;

said hypotube includes a formed distal open end tapered radially inwardly; and said core wire includes a sawtooth wave-shaped diametrically offset portion formed to effect a continuous friction fit through said formed passage and within said hypotube and to lock in said tapered end and define a locking mechanism.

7. A guidewire according to claim 4 wherein:

said hypotube includes an interior surface formed into a polygonal cross-sectional shape; and said core wire is formed with a polygonal cross-section for close-fitting slidable axial receipt within said hypotube to prevent relative rotation between said hypotube and said core wire and provide enhanced torsional stiffness through said intermediate section.

8. A guidewire according to claim 1 wherein:

said flexible portion comprises a formed hypotube having an interior bore closed at the distal extremity of said intermediate section; and said stiffener comprises a relatively stiff wire.

9. A guidewire according to claim 8 wherein:

said hypotube is fixed; and said core wire is moveable within said internal bore.

10. A guidewire according to claim 8 wherein:

said internal bore is of a constant diameter; and said core wire is of a constant diameter.

11. An angioplasty guidewire comprising:

a proximal shaft for insertion into a patient's body and having a distal end;

an intermediate section extending axially outwardly from said distal end of said shaft to a distal joint, said intermediate section including a spring coil, a hypotube extending from said proximal shaft having a formed distal open end tapered radially inwardly to define a restricted mouth and a flexible core wire formed with a medial portion complementally formed to selectively engage said mouth and form a friction fit, said core wire slidably received in said hypotube and anchored to said distal joint, said hypotube being coaxially disposed over said core wire and said hypotube and said core wire being slidable relative to each other to cooperatively impart a variable stiffness to said intermediate section, said variable stiffness being increased by advancing said hypotube over said core wire toward said distal joint, said variable stiffness being reduced by moving said hypotube over said core wire away from said distal joint; and a flexible distal tip mounted to an end of said intermediate portion at said distal joint and projecting axially therefrom.

12. A guidewire according to claim 11 wherein:

said medial portion is formed with a radially inwardly directed taper to engage said hypotube mouth.

13. A guidewire according to claim 11 wherein:

said medial portion is formed with a sawtooth wave-shaped diametrically offset portion formed to engage said hypotube mouth.

14. A method of deploying a guide wire through a vasculature to a restricted location in a blood vessel, said guide wire including a proximal shaft for insertion into a patient's body having a distal end; an intermediate section extending axially outwardly from said distal end of said shaft to a distal joint, said intermediate section comprising a spring coil, a flexible member and a stiffener extending from said proximal shaft, said stiffener being coaxially disposed over said flexible member and said stiffener and said flexible member being slidable relative to each other; said guide wire further including a flexible distal tip mounted to the end of said intermediate portion at said distal joint and projecting axially therefrom, said method including the steps of:

shifting said flexible member and stiffener into an initial position of said guide wire to effect a predetermined flexibility in said intermediate section;

inserting said guide wire through an incision accessing said vasculature;

threading said guide wire through said vasculature to said restricted location; and stiffening said intermediate section by axially displacing said stiffener with respect to said flexible member toward said distal joint sufficient to support a dilatation catheter.

15. A method of deploying a guide wire according to claim 14 wherein said threading step includes:

locking said flexible member and stiffener to inhibit relative rotation therebetween and increase the torsional stiffness of said guide wire.

* * * * *